Figure 1:
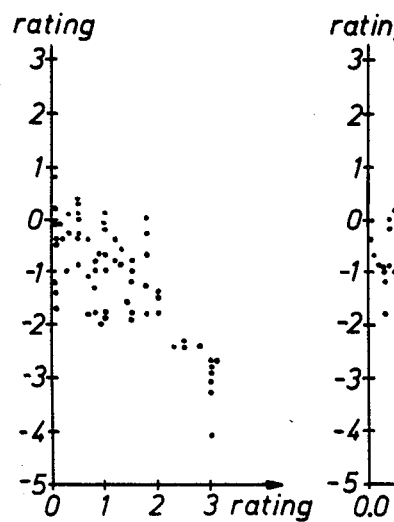

United States Patent [19]

Mortensen

[11] Patent Number: 4,563,428

[45] Date of Patent: Jan. 7, 1986

[54] METHOD OF DETECTING OBNOXIOUS TAINT SUCH AS BOAR TAINT IN INDIVIDUAL ANIMAL BODIES, PREFERABLY CARCASSES OR PARTS THEREOF

[75] Inventor: Anna B. Mortensen, Roskilde, Denmark

[73] Assignee: Slagteriernes Forskningsinstitut, Roskilde, Denmark

[21] Appl. No.: 502,020

[22] PCT Filed: Sep. 8, 1982

[86] PCT No.: PCT/DK82/00080

§ 371 Date: May 6, 1983

§ 102(e) Date: May 6, 1983

[87] PCT Pub. No.: WO83/00928

PCT Pub. Date: Mar. 17, 1983

[30] Foreign Application Priority Data

Sep. 9, 1981 [DK] Denmark ............................ 3981/81

[51] Int. Cl.$^4$ ...................... G01N 33/12; G01N 21/78
[52] U.S. Cl. .......................................... 436/21; 436/96
[58] Field of Search ...................... 356/407, 408, 411; 436/21, 96, 111, 128, 131, 129, 106, 817

[56] References Cited

U.S. PATENT DOCUMENTS

| | | | |
|---|---|---|---|
| 3,422,271 | 1/1969 | Fuhrmann | 356/411 X |
| 4,158,546 | 1/1979 | Lam et al. | 436/97 |
| 4,263,512 | 4/1981 | Sagusa et al. | 356/407 X |
| 4,384,206 | 5/1983 | Bjarno | 436/96 X |
| 4,405,718 | 9/1983 | Rapkin et al. | 436/96 X |

FOREIGN PATENT DOCUMENTS 1057997 2/1967 United Kingdom .

OTHER PUBLICATIONS

Cant et al., A Routine Method for Determining Indoles in Butter and Milkfat, CA93(9)93634t, 1980.
Hansson et al., The Importance of Androstenone and Skatole for Boar Taint, CA95(1):5277s, Swedish J. Agric. Res/. 10, 167–173/1980.
Siggia, Quantitative Organic Analysis via Functional Groups, Wiley and Sons, pp. 514–517, 1963.
Internation Publication No. 80/02597, by Bjarno (PCT) pp. 1–22, w/ search report.
"A Radioimmunoassay for 5a-Androst-16-3-One in Porcine Adipose Tissue", by O. Andresen, Acta Endocr., 79, 619–624/1975.

*Primary Examiner*—Barry S. Richman
*Assistant Examiner*—Michael S. Gzybowski
*Attorney, Agent, or Firm*—Fleit, Jacobson, Cohn & Price

[57] ABSTRACT

Boar taint in individual animal bodies, preferably carcasses or parts thereof, is detected by preparing an extract of a meat and/or fat sample from the body or part thereof, reacting said extract with a color reagent, for which the color intensity developed at certain wavelengths exhibit a statistical relationship with boar taint, determining the transmittance or absorbance of the reacted extract at one or more such wavelengths, and inserting the recorded values in the said statistical relationship. A high correlation has been found to exist between color reaction and boar taint evaluation so that the transmittance or absorbance at wave lengths characteristic of the color reaction gives a quantitative measure of boar taint intensity. This has made it possible to determine threshold values which objectively define organoleptic inacceptable taint levels. The method is fast and accurate and requires no extensive work; in addition it has been possible to automatize it so that it can be used directly in connection with slaughter lines in slaughterhouses for industrial control and sorting of individual carcasses.

16 Claims, 3 Drawing Figures

METHOD OF DETECTING OBNOXIOUS TAINT SUCH AS BOAR TAINT IN INDIVIDUAL ANIMAL BODIES, PREFERABLY CARCASSES OR PARTS THEREOF

The present invention relates to a method of detecting obnoxious taint such as boar taint in individual animal bodies, preferably carcasses or parts thereof, in which spectrophotometric parameters statistically related to such taint are determined for the individual body.

Meat cuts from boars can develop an unpleasant odour, so-called boar taint, during and after cooking. In contrast, such obnoxious taint rarely occurs when cuts from castrated boars are cooked. Thus, male pigs are usually castrated when young, in order to avoid obnoxious taint in the cooking of the meat in the household. Similar problems may arise in other species such as cattle, sheep and goats.

Castration of male pigs, however, is vitiated by a decrease in the feed utilization, an increase in the frequency of diseases, and also a reduced meat percentage in the carcasses.

Generally androstenone (5α-androst-16-ene-3-one) is considered to be the main contributor to boar taint. But several studies indicate that other factors, too, i.a. skatole, contribute to boar taint. K. E. Hansson, K. Lundström, S. Fjelkner-Modig and J. Persson: "The Importance of Androstenone and Skatole for Boar Taint", Swedish J. Agric. Res. 10, 167–173 (1980), investigated boar taint intensity and the concentrations of androstenone, indole and skatole in samples from back fat taken from a number of boars, and some castrates and gilts, at slaughter. Androstenone in fat was determined according to the extraction and radioimmunological procedure described by Ø. Andresen, Acta Endocr. 79, 619–624 (1975). Skatole and indole were isolated from fat by steam distillation and extraction into n-pentane and analyzed by gas liquid chromatography, a very sophisticated and time-consuming procedure. The recovery of skatole was only 44–47%. They found an overall correlation between boar taint and androstenone in boars of 0.60 and a correlation between boar taint and skatole of 0.53, both with a level of significance of $p \leq 0.001$. The overall correlation between boar taint and indole was only 0.26 with a level of significance of $p \leq 0.05$. At the end of their paper the authors say that as far as is known at present, androstenone and skatole both contribute to boar taint, and their results indicate that skatole contributes to a somewhat lesser extent than androstenone. They mention that according to other studies fatty acid composition too has a certain influence, and conclude that further investigations are needed to establish whether other substances are important for the intensity of the taint; it might then be possible to develop a rapid and instrumental method of analysis.

Methods have been proposed for detecting whether individual carcasses will develop boar taint when cuts from them are cooked so that it will be possible to sort out these carcasses before the further processing into cuts intended for the retail trade, and to use the sorted carcasses industrially, e.g. for canned food or sausages where boar taint is not important.

Thus, it is proposed in PCT/DK80/00028 to sort non-castrated boar carcasses on the basis of IR spectrophotometric transmission data for a fat sample from the carcass, there being a statistical relationship between a subjectively determined boar taint in a sample from a carcass and the transmittance of a fat sample from the carcass, measured in the infrared region. However, the method is not so reliable that the sorting can be based on the method alone, there being a not insignificant risk that carcasses which develop boar taint when cooked will pass the control. Accordingly, it is proposed in that application to determine one or more additional parameters statistically related to boar taint, e.g. the concentration of unsaturated fatty acids in the fat sample, and to use the data thus obtained together with the IR spectrophotometric data for detection of boar taint in the individual carcass. However, with these methods there is still a considerable risk of tainted carcass cuts being delivered to the retail trade, or the known supplementary analyses are of such type that they cannot be carried out on an industrial scale. For example, the art comprises several methods for detection of androstenone, which is believed to constitute an important factor in boar taint, but these methods are slow and laborious and can therefore not be used either separately or jointly with the IR method defined in the above PCT application to detect boar taint in carcasses advanced on a slaughter line.

The object of the present invention is to provide an industrially useful method of the type stated in the opening paragraph, which enables a more reliable detection of boar taint than the above-mentioned IR method, either when used alone or together with other industrially useful methods for boar taint detection.

This object is achieved according to the invention by a method, which is characterized by preparing an extract of a meat and/or fat sample from the body or part thereof in question, reacting said extract with a colour reagent for which the colour intensity developed at certain wavelengths exhibit a statistical relationship with obnoxious taint, determining the transmittance or absorbance of the reacted extract at one or more such wavelengths, and inserting the recorded values in the said statistical relationship.

Thus, the method of the invention provides an extract containing substances which are characteristic of boar taint, and these substances are "developed" by means of a colour reagent. Surprisingly, a high correlation has been found to exist between colour reaction and boar taint so that the transmittance or absorbance at wavelengths characteristic of the colour reaction gives a quantitative measure of boar taint intensity. This has made it possible to determine threshold values which objectively define organoleptic inacceptable taint levels so that it can be detected by the method of the invention, whether cuts from an animal body will develop boar taint under cooking. The method is fast and accurate and requires no extensive work; in addition, it has been possible to automatize it so that it can be used directly in connection with slaughter lines in slaughterhouses.

Throughout this specification with claims the term "colour" is to be taken in a broad sense as denoting spectral absorption not only in the visible range, but also in the infrared and ultraviolet ranges of the electromagnetic spectrum.

The spectrophotometric data of the reacted extract of a meat and/or fat sample from an individual animal body or a part of it may be spectral absorbance at one or more wavelengths, at least one of which is characteristic of the reaction product between the colour reagent and one or more compounds in the extract which are statistically related to boar taint. The other wavelengths may serve as references.

The spectrophotometric data of the reacted extract may also be the corresponding transmittance of light through the sample at one or more corresponding wavelengths.

The transmittance and/or absorbance may be determined from the transmission at specific wavelengths in relation to the transmission measured on a standard solution. For example, a measurement may be taken in relation to a dilution series of a solution containing a known amount of the reaction product between the colour reagent used and one or more compounds which are statistically related to boar taint in animal bodies.

The transmittance and/or absorbance of the reacted extract can also be determined from the difference or the ratio between the transmissions of the extract at several predetermined wavelengths, some of which are characteristic of boar taint, while others may be unrelated to boar taint and serve as references. This procedure may serve to control the analytical stability of an automatic system for influence of air bubbles, deviations in the composition or characteristics of the added reagents etc.

The method of the invention can be carried out in a short period of time, e.g. within 10 to 20 minutes, while the carcass continues to be processed on a slaughter line. Therefore, by means of the method of the invention it can currently be determined on the slaughter lines whether the individual carcasses will develop boar taint so that the tainted carcasses may be sorted out e.g. so as to be used in certain processed meat, while the other carcasses after chilling can be used for any purposes, particularly fresh pork and bacon.

Sampling from the carcasses can take place at any point along the slaughter line, but preferably not further ahead on the line than the result of the examination is available before the carcasses reach the sorting point, e.g. before being admitted to the chilling room. Expediently, samples can be taken e.g. in connection with measurements of the meat percentage (classification) of the carcass so that the samples can be prepared and analysed before the carcass is transferred to the chilling room. Sampling can be effected manually, semi or fully automatically, e.g. in connection with the use of classification equipment.

It should be noted that the time and temperature conditions from the sampling until the actual preparation of the extract might influence the analysis results, and so these conditions must be standardized. In case of failure of the analyzing equipment it might thus be necessary to prescribe freezing of the samples.

The preparation, analysis and numerical processing of the result of the analysis should be carried out semi or fully automatically as manual processing and determination of e.g. 100 to 400 samples per hour would be very laborious. For example, automatic analyses can be carried out according to the so-called air segmented continuous flow system or by flow injection analysis.

Even though a large number of samples per hour is to be processed, there will be sufficient time for preparing each sample before the analysis when the analysis instrument is suitably constructed.

Using an extract reacted with a colour reagent to determine the spectrophotometric data, as described, it is possible by selection of colour reagent and/or extracting agent to eliminate the influence of substances which are not statistically related to boar taint, but disturb the measurement of the substances which are interesting in connection with boar taint. It may e.g. be substances which disturb because they have a colour in the same wavelength range as the substances to be detected by the method of the invention, or consume the added colour reagent, or it may be particles that scatter the light which illuminates the sample.

It has been found that a sample of such purity as allows it to be reacted with the colour reagent can be prepared sufficiently rapidly by extraction of meat and/or fat samples, providing a sufficiently unequivocal reaction for it to be detected with adequate reliability by spectrophotometric determination whether individual animal bodies will develop boar taint.

To extract the meat and/or fat samples, solvents or mixtures of solvents are used which dissolve one or more of the substances contributing to boar taint or specifically accompanying tainted animal bodies. The solvents dissolve or possibly also open up the components in which these substances are bound. The extraction is preferably carried out at a temperature from about $-1°$ to about $25°$ C.

It has been found that tainted meat and/or fat samples contain substances which are specific to these samples and are soluble in polar organic solvents, and which can be reacted with a colour reagent in these solvents.

Accordingly, an embodiment of the method of the invention is characterized by using an extracting agent containing a polar organic solvent, in particular acetone, for the extraction. According to an embodiment of the method, the ability of the extracting agent to dissolve disturbing lipid substances can be reduced by using an extracting agent comprising a mixture of a polar organic solvent and water, in particular a water/acetone mixture, for the extraction. A suitable mixture of solvents can thus consist of an acetone/water mixture, e.g. in a ratio from 2:1 to 10:1.

The solubility of the water soluble or partly water soluble substances contained in the meat and/or fat sample can depend upon the pH, and polar solvents are therefore preferably admixed with a buffer which ensures reproducibility, optimizes the solubility of the substances characteristic of boar taint, and/or reduces the solubility of undesirable substances, e.g. unspecific colouring substances or dispersed substances.

Accordingly, an embodiment of the method of the invention comprises using an extracting agent for the extraction which contains a buffer, in particular an extracting agent adjusted to a pH of 7–8 by means of a buffer. In the stated pH range substances characteristic of boar taint enter into the extracting agent.

Thus, to extract meat and/or fat samples it has been found particularly advantageous to use a solvent mixture of acetone and an aqueous buffer solution adjusted to a pH of 7–8, preferably 7.2–7.8, and in particular around 7.5, because this provides for solution of substances which are characteristic of boar taint without the extract being vitiated by a great content of fats.

Furthermore, the water-containing extracting agents may be admixed with surfactants which improve the water solubility of the substances characteristic of boar taint. For the extraction may be used an extracting agent containing as the buffer an aqueous solution of an organic buffer substance, e.g. tris-(hydroxymethyl)aminomethane which simultaneously acts as a surfactant. The buffer solution may be adjusted to the desired pH by means of an ordinary acid or base, e.g. hydrochloric acid or sodium hydroxide solution. Organic solvent and buffer solution can be mixed in proportions adapted to the substances it is specifically desired to extract or retain in the meat and/or fat sample, it being possible e.g. to mix acetone and buffer solution in a ratio of between 2:1 and 10:1. Fat samples are expediently extracted by using a mixture containing relatively much water, e.g. acetone and water in the ratio 3:1, while relatively little water, e.g. acetone and water in the ratio 9:1, can be used for the extraction of a meat sample.

To protect oxygen sensitive substances during and after the extraction of the meat and/or fat sample, the method may be effected in an inert atmosphere. However, the extracting agent may be admised with a reducing agent retarding the reaction between oxygen in the air and oxygen sensitive colour responsive substances characteristic of boar taint before, during or after the extraction. An embodiment of the method of the invention therefore comprises using for the extraction an extracting agent containing a reducing agent, or adding a reducing agent to the extract.

A meat and/or fat sample can be extracted in the usual manner, e.g. by mincing the sample during mixing with the extracting agent and then clarifying the mixture to remove undissolved fat, cellular components, connective tissue and the like. The extract may optionally be purified so that extracted tainting substances may additionally be freed of disturbing substances.

The expression "colour reagent" should be taken to include any compound or mixture of compounds which in the extract reacts with one or more compounds statistically related to boar taint in animal bodies, to form a coloured product.

The colour reagents used are preferably compounds which in the extract specifically react with compounds accompanying boar taint. However, it is also possible to use colour reagents which in the extract additionally react with compounds having no bearing on boar taint and possibly forming coloured compounds, provided that they do not cause blurring of the bands which are characteristic of the reaction product between the colour reagent and boar taint accompanying compounds.

Colour reagents may be used which are known to react with specific compounds which have previously been specifically shown in connection with boar taint, e.g. androstenone. However, it is not required that the specific compounds occurring in tainted animal bodies are known. Thus, a colour reagent may be used which by tests has been shown to cause a specific colour change when added to extracts of meat and/or fat samples from tainted animal bodies.

The tests on which the invention is based show a statistical relationship between spectrophotometrical data of an extract reacted with a colour reagent for amines, including heterocyclic nitrogen compounds such as indoles, and boar taint in carcasses from which the extract has been prepared. Accordingly, an advantageous embodiment of the method of the invention is characterized by reacting the extract with a colour reagent for amines, including heterocyclic nitrogen compounds.

It was found in the tests referred to that extracts prepared from samples from tainted carcasses assume a stronger red colour than extracts prepared from non-tainted carcasses when the extracts are reacted with a colour reagent comprising p-dimethylaminobenzaldehyde. An embodiment of the method of the invention is therefore characterized by reacting the extract with a colour reagent comprising p-dimethylaminobenzaldehyde.

A more specific embodiment of the method of the invention comprises determining the transmittance or absorbance in the wavelength range of 540 to 600 nm on an extract reacted with a colour reagent comprising p-dimethylaminobenzaldehyde.

Colouring specific to tainted carcasses occurs in a water/acetone extract admixed with a colour reagent comprising p-dimethylaminobenzaldehyde. An embodiment of the method of the invention is therefore characterized by determining the transmittance or absorbance in the wavelength range of 540 to 600 nm on an extract which is produced by extraction with an extracting agent comprising water and acetone in a ratio between 2:1 and 10:1 by volume and reacted with a colour reagent comprising p-dimethylaminobenzaldehyde.

The extract can be reacted with the colour reagent by dropwise addition of the colour reagent to the extract in the measuring cuvette, with stirring or shaking.

The solution of colour reagent or the extract may optionally contain auxiliary substances, such as a strong acid and an alcohol. An embodiment of the method of the invention is accordingly characterized by carrying out the reaction with a p-dimethylaminobenzaldehyde reagent in the presence of a strong acid and an alcohol.

After the reaction the extract may be left to stand for a specific period of time so that the resulting "colourant" can spread and stabilize.

In the method of the invention the transmittance or absorbance of an extract of a meat and/or fat sample reacted with a colour reagent is determined by means of an apparatus designed to conduct a spectrophotometric measurement. Thus, the apparatus may comprise a spectrophotometer capable of illuminating and measuring the sample at one or several wavelengths, or even by scanning the absorption spectrum of the sample, and it may also be provided with auxiliary devices, such as polarizing filters.

The apparatus used in the method of the invention may also comprise a control and computing unit in which is decided by means of a program, which parameters are to be determined, and which setting the spectrophotometer is to have during the measurement in question, and in which the measured data together with any other data, e.g. relating to weight, are successively stored and processed, after collection of the required number of data, in accordance with a predrafted model to decide whether the carcass is tainted.

Even though the method of the invention has mainly been described in connection with sorting of carcasses of non-castrated boars, the method can also be used for sorting carcasses of gilts on the slaughter line, if desired. However, testing of both boars and gilts for boar taint will on an average double the sampling frequency.

The method of the invention can moreover be used in connection with breeding for the purpose of separating the boars and sows mainly responsible for boar taint in their offspring. Breeding may be based solely on the boar taint in the offspring. However, the selection can also be made in consideration of the boar taint of the parents as well as the offspring, optionally already while alive.

The method of the invention is also applicable to detect obnoxious taint in other species such as cattle, sheep and goats.

The method of the invention will be illustrated in greater detail by the following examples.

EXAMPLE 1

From carcasses of boars were taken belly or backfat samples sufficiently large to be divided into several small samples for taint evaluation and extract preparation.

Taint evaluation

About 5 g of fat sample are heated slowly in a flask on a hot plate. During heating, a panel of three or four trained members judge the degree of boar taint from the sample according to a 3-point scale, where
0 = no boar taint
½ = doubtful
1 = slight boar taint
2 = some boar taint
3 = strong boar taint

Colouring, spectrophotometrical measurement

An 0.2M aqueous solution of tris-(hydroxymethyl-)aminomethane ("Tris") is adjusted to a pH of 7.5 and admixed with 1% of a 0.1M aqueous sodium sulfite solution. The solution is mixed with acetone in the ratio of 1:3. An amount of 5 g of fat is weighed out and mixed with 10 ml of this solution during mincing of the sample, and the mixture is then filtrated. The filtrate is topped up with the above buffer solution to a volume of 10 ml.

Colour reagent is prepared by dissolving 0.5 g of p-dimethylaminobenzaldehyde in 20 ml of strong sulfuric acid (6 vol. of concentrated sulfuric acid +1 vol. of water) carefully added to 30 ml of 99,9% ethanol and cooled to room temperature.

1 ml of colour reagent thus produced is mixed with 1 ml of filtrate, and after 5 minutes' standing the transmission is measured on a spectrophotometer at 580 nm, a control measurement being effected at the same time on a correspondingly produced blank. A spectrophotometer of the Zeiss PL4 make is used. The transmission is converted into absorbance.

The absorbance of solutions containing 0.1, 0.2, 0.4 and 0.6 µg of skatole/ml and reacted with the colour reagent is found in a similar manner. The absorbance is plotted as a function of the skatole concentration in a standard curve.

The content of skatole equivalents in the fat sample can then be read on the standard curve against the absorptance of the sample.

Results

The results of the fat sample measurements are tabulated in table I below, in which the corresponding taint evaluation results are listed. It will be seen that there is a distinct correlation between the taint evaluation of the samples and the skatole equivalents.

TABLE I

| Sample no. | Taint eval. | Skatole equivalents (ppm) | Sample no. | Taint eval. | Skatole equivalents (ppm) |
|---|---|---|---|---|---|
| 1 | 0.09 | 0.01 | 22 | 0.8 | 0.04 |
| 2 | 1.5 | 0.01 | 23 | 1.3 | 0.07 |
| 3 | 1.3 | 0.00 | 24 | 1.0 | 0.08 |
| 4 | 1.2 | 0.06 | 25 | 1.3 | 0.08 |
| 5 | 0.5 | 0.01 | 26 | 3.0 | 0.40 |
| 6 | 1.4 | 0.04 | 27 | 3.0 | 0.21 |
| 7 | 2.0 | 0.07 | 28 | 1.5 | 0.04 |
| 8 | 1.2 | 0.05 | 29 | 2.0 | 0.04 |
| 9 | 0.2 | 0.04 | 30 | 2.0 | 0.14 |
| 10 | 1.3 | 0.09 | 31 | 3.0 | 0.62 |
| 11 | 0.7 | 0.09 | 32 | 0.8 | 0.01 |
| 12 | 0.7 | 0.04 | 33 | 1.0 | 0.04 |
| 13 | 0.7 | 0.06 | 34 | 0.5 | 0.04 |
| 14 | 0.0 | 0.04 | 35 | 1.0 | 0.01 |
| 15 | 1.7 | 0.09 | 36 | 1.6 | 0.08 |
| 16 | 1.8 | 0.15 | 37 | 0.9 | 0.05 |
| 17 | 2.5 | 0.27 | 38 | 0.3 | 0.04 |
| 18 | 2.8 | 0.37 | 39 | 0.3 | 0.06 |
| 19 | 3.0 | 0.07 | 40 | 1.3 | 0.05 |
| 20 | 1.8 | 0.10 | 41 | 1.5 | 0.03 |
| 21 | 1.8 | 0.12 | | | |

The correlation between skatole equivalents and taint evaluation can be calculated to 0.66 from table I.

The origin of the carcass material used varies greatly, since samples of eight gilts are used as a control (sample No. 1, 2, 9, 12, 14, 37, 39 and 40), and the boar samples originate from several different producers' herds and different feeding systems. The method must thus be considered to be insensitive to variations of the abovementioned type.

EXAMPLE 2

In this example samples from a plurality of pigs were subjectively evaluated for taint by a tasting panel of 9 housewives having no connection to the test laboratory and a laboratory team of 3 to 5 employees at the test laboratory, respectively; these subjective taint evaluations were compared with analyses of the same samples by the method of the invention.

The tasting panel's evaluations were performed on a slice of salted streaky bacon heated in a closed Petri dish in an oven until the fat seethed but was not burned, and the taint, taste and overall impression were then evaluated according to a scale with ratings from +5 to −5, the negative part of the scale indicating increasing boar taint, ill-taste and bad overall impression, respectively.

The laboratory team's evaluations were performed on a pure fat sample heated in a 100 ml flask and examined a few times during the heating process. Taint ratings were given according to the following scale: 0 = no boar taint, 1 = slight boar taint, 2 = some boar taint, 3 = strong boar taint.

The analyses were performed on fat samples as a spectrophotometric determination of a substance (or several) which reacts like skatole by extraction with an organoaqueous agent and reaction with a p-dimethylaminobenzaldehyde reagent and was therefore measured in relation to skatole. In the following this analysis of skatole equivalent is called "skatole analysis". The analyses were performed automatically by means of an equipment composed of various "Technicon" components.

REAGENTS

Extracting agent

An 0.1M "Tris"-buffer solution is prepared by dissolving 60.59 g of tris-(hydroxymethyl)-amino-methane ("Tris") in distilled water, diluting to 5 l, and adjusting the pH to 7.5 with conc. HCl (about 30 ml). An 0.1M $Na_2SO_3$ solution is prepared by dissolving 12.6 g of sodium sulfite in distilled water and diluting to 1 liter. 3 liters of acetone (p.a.) and 1 liter of "Tris"-buffer are mixed, and 40 ml of 0.1M $NaSO_3$ are added. In the following this extracting agent is referred to as "acetone-"Tris" (3:1)".

Colour reagent 8 g of p-dimethylaminobenzaldehyde are dissolved in 480 ml of 99.9% ethanol (p.a.). To the solution are added 320 ml of $H_2SO_4$ (conc. $H_2SO_4$/dist. $H_2O$, 3:1 by volume) slowly with cooling. If the colour reagent is to be used in a continuous flow system, 8 ml of 30% "Brij-35" are added to decrease the surface tension. The colour reagent is stored in a dark bottle in a refrigerator, and the bottle is evacuated before use.

Standard 1 mg of skatole (3-methylindol) in 1 liter of acetone-"Tris" (3:1). It is essential that all reagents are analytical grade. The mixture of acetone and "Tris"-buffer has to be accurate; 1–2% acetone more or less is liable to cause faulty results.

PROCEDURE 4 g of backfat are weighed in a beaker and placed in the solid preparation sampler of the equipment. The sample is minced and mixed with 40 ml of acetone-"Tris" (3:1). A small portion of the extract is passed through the air segmented continuous flow system of the equipment in which it is filtered, vented to expel entrapped air bubbles and then, at a rate of 0.60 ml/min., added to 0.85 ml/min. of the colour reagent. After a holding period of 3–5 minutes for colour development, the absorbance of the reacted extract sample at 580 nm is measured in the spectrophotometer of the equipment.

The analyzing system is calibrated against a blank of acetone-"Tris" (3:1) and against 4 ml of the standard solution of 1 ppm skatole in acetone-"Tris" (3:1), so that the measured values are recorded directly in ppm of skatole equivalents.

Acetone-"Tris" (3:1) and colour reagent must be kept cold; acetone to prevent evaporation during mixing, and colour reagent to remain stable.

The samples must be fresh since free amino acids are formed in non-fresh, rancid or sour samples, and these free amino acids may cause colour reaction with p-dimethylaminobenzaldehyde reagent and thus produce false positive results.

TEST MATERIAL (1) 60 boar samples +5 gilt samples from slaughter pigs (about 65 kg of slaughter weight). The boars were produced in ordinary herds and reared together with gilts. They were cross breeds (mainly LYL).

(2) 100 boar samples from slaughter pigs (about 65 kg of slaughter weight).

(3) 44 boar samples from progeny test pigs of ordinary slaughter-size (about 65 kg).

In the slaughtering belly cuts were taken for analysis. The cuts were divided as shown by the following figure.

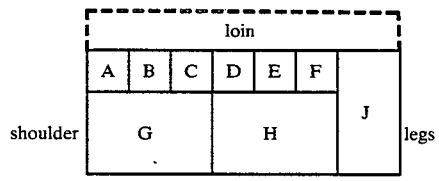

The loin was not included. Skatole analysis was carried out on one of the sub-cuts A–F and compared with the taint evaluation on G or H.

In the following results the level of significance of the correlation calculations are stated as *, , *, and $^{NS}$ for $p<0.001$, $p<0.01$, $p<0.05$ and non-significant, respectively.

RESULTS

Reliability of boar taint evaluation

Generally, boar taint evaluation is performed by means of a small laboratory team as stated in the foregoing. The reliability of this evaluation and the question of whether the evaluation is representative for ordinary consumer responses, are initially elucidated by comparing the results of the laboratory team's and the tasting panel's evaluation of sample series 1 (65 samples, 5 of them gilts) and submitting 15 of the samples to the tasting panel two times, without the judges having been informed of the double determination.

In the double determinations there was, apart from a single sample, good correlation between the first and the second evaluation, each result being the average of 9 judges' evaluation. The correlation between the two evaluations was calculated at $r=0.80$ for the tasting panel as a whole (average of 9 tasters).

The comparison between the tasting panel's and the laboratory team's evaluation results (60 boars and 5 gilts) gave the following correlation.

| Laboratory team | Tasting panel | Correlation |
|---|---|---|
| taint | taint | $r = -0.76$*** |
| taint | taste | $r = -0.69$*** |
| taint | overall impression | $r = -0.70$*** |

Thus, there is by and large the same correlation between the two panels' evaluation of taint as between the tasting panel's double determination. A comparison between the two evaluations is shown in FIG. 1.

The laboratory team considered that all samples rated 2.5 and upwards should be rejected. The tasting panel found (having evaluated all samples) that the samples with a rating of less than −2 were inacceptable. As appears from FIG. 1 there is close agreement between the samples rejected by the tasting panel and the laboratory team.

It may thus be concluded on the basis of these examinations that taint can be evaluated just as well by a laboratory team as by a large tasting panel, and that the two smelling panels apparently react in the same manner to the tainted samples. It also appears that the repeatability in the taint evaluation is of the order $r=0.8$.

Reliability of skatole analysis

Double analysis was performed on 120 samples from sample series 1 and 2. The double analyses were performed on the same day, and the samples were analysed in series of 6 to 12 and then repeated with the samples in the same sequence. This gave a correlation between the first and the second determination of $r=0.94$. Residual error (standard deviation) is 0.036 ppm. This means that the analysis results should be stated ±0.04 ppm. Using double determination the standard deviation might be reduced by 0.015 ppm, and so a single determination will suffice.

10% of the 120 samples is characterized as tainted in both series of analysis. However, there is one sample which has been moved from tainted to non-tainted from the first to the second analysis, and one which has been moved from non-tainted to tainted.

The recovery of skatole in this automatic procedure was determined by injecting a predetermined amount of skatole in fat samples previously analyzed. The fat samples were then analyzed once more, and the percent recovery of the injected skatole was calculated from the difference between the two analyses in relation to the injected amount. The recovery was found to be 95-105%.

Comparison of taint evaluation by tasting panel and skatole analysis

Skatole equivalents were analysed in the 60 boar and 5 gilt samples from sample series 1.

The correlation between the tasting panel's taint evaluation and the skatole analyses is r=0.65 ***.

Figure 2:
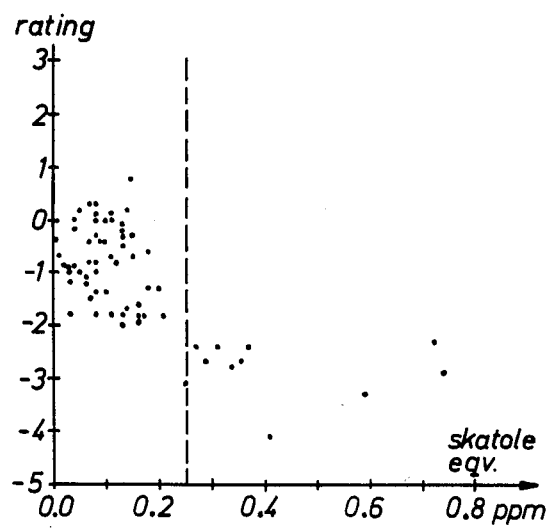

As appears from FIG. 2 a skatole content of 0.25 ppm and upwards corresponds to a rating of below −2.0. This material of 60 boars does not include any which has been classified wrongly by sorting according to a single skatole analysis and a limit of 0.25 ppm.

Taint evaluation by laboratory team and skatole analysis on all samples

Taint evaluation by the laboratory team and skatole analysis were performed on sample series 1, 2 and 3, a total of 204 boar samples.

Figure 3:
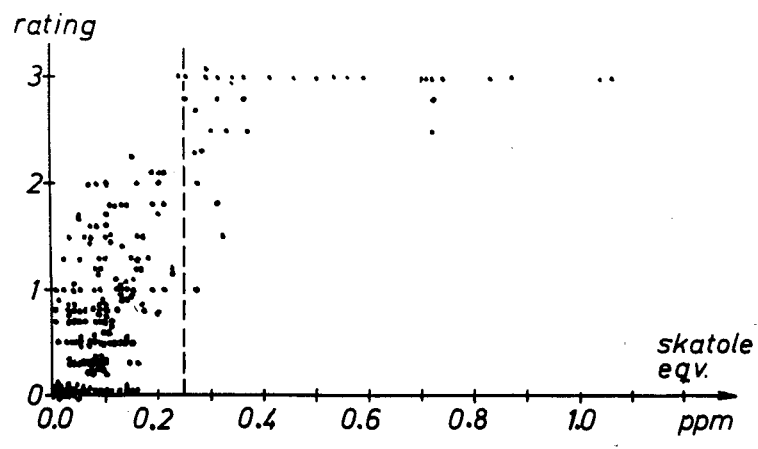

FIG. 3 shows the correlation between analysis and evaluation.

The correlation between evaluation and analysis is r=0.73***.

The correlation is the same for the whole material (204 samples) and for the 160 slaughter pigs (i.e. without progeny test pigs), even though the frequency of samples tainted is much higher among the progeny test pigs than among the slaughter pigs.

This material comprises a few pigs which would be rejected by analysis and which were not rejected by the laboratory team (about 3%).

All samples rejected by the laboratory team are rejected by the analysis (0.25 ppm and upwards).

If the correlation coefficients are arranged according to order the result will be as follows:

| | |
|---|---|
| Tasting panel, double determination | r =0.80***, n = 15 |
| Tasting panel - laboratory team | r = −0.76***, n = 60 |
| Laboratory team - skatole analysis | r = 0.73***, n = 204 |
| Tasting panel - skatole analysis | r = 0.65***, n = 60 |

It appears from this that the best evaluation of taint is an entire tasting panel's evaluation or a trained laboratory team's evaluation. The correlation between a single analysis of skatole and the taint evaluation is almost quite as high as between two taint evaluations.

Variation of skatole analyses in belly cuts

As explained in the foregoing, belly cuts were taken from each individual animal; skatole analysis was carried out on one of the sub-cuts A-F, and taint evaluation was performed on one of the sub-cuts G or H.

To demonstrate variations, if any, in skatole analysis and taint evaluation within the individual cut, some of the remaining G and H cuts were subjected to as many analyses as allowed by the available amount of fat. A total of 11 cuts were tested, and for each cut 5 samples spaced diagonally across the cut were taint-evaluated by the laboratory team, while the remaining 20 samples were analyzed. The results were treated statistically and showed no difference within the individual cuts.

I claim:

1. A rapid and reliable method of detecting obnoxious taint in individual animal bodies, comprising the steps of:
   preparing an extract of a meat and/or fat sample from a selected body or part thereof, said extract being obtained by using a polar solvent as an extraction agent to dissolve constituents of said meat and/or fat sample which are associated with obnoxious taint while substantially excluding constituents of said meat and/or fat sample which interfere with said method of detecting obnoxious taint;
   reacting said extract with a coloring agent comprising p-dimethylaminobenzaldehyde to detect constituents of said meat and/or fat sample which indicate the presence of said obnoxious taint;
   determining the transmittance or absorbance of the reacted extract at a wavelength in the range of 540 to 600 nm; and
   detecting obnoxious taint in the selected body or part thereof based on the determined transmittance or absorbance of the reacted extract, said method of detecting obnoxious taint being completable within a time of about 10 to 20 minutes.

2. A method according to claim 1, wherein the transmittance of absorbance of the reacted extract is compared with a predetermined threshold value, and the selected body or part thereof is evaluated relative to the threshold value.

3. A method according to claim 1 wherein, a fat sample taken from a newly slaughtered carcass is used.

4. A method according to claim 1, wherein the steps are carried out at a temperature from about −1° to about 25° C.

5. A method according to claim 1, wherein the extract obtained contains a reducing agent.

6. A method according to claim 1, wherein the reaction with p-dimethylaminobenzaldehyde is effected in the presence of a strong acid in an alcohol.

7. A method according to claim 1, wherein the extract is obtained using a mixture of acetone and water in a ratio of from about 2:1 to about 10:1 by volume.

8. A method according to claim 1, wherein the transmittance and/or absorbance measurements of the reacted extract are determined from differences or the ratio between the transmission of the extract at one or more wavelengths in the range of 540 to 600 nm which are characteristic of the colour reaction and the transmission at one or more reference wave lengths which are indifferent to the colour reaction.

9. A method according to claim 8, wherein a transmittance or absorbance measurement is determined by comparing transmission at a wavelength in the range of 540 to 600 nm to a transmission at a different wavelength in the range of 605 to 650 nm.

10. A method according to claim 1, wherein said polar solvent is a mixture of water and acetone.

11. A method according to claim 10, wherein the mixture contains a buffer, to adjust its pH to 7-8.

12. A rapid and reliable method of detecting obnoxious taint in individual animal bodies which is completable within about 10 to 20 minutes, said method comprising the steps of:
  (a) extracting a fixed amount of fat sample taken from a selected animal body with an about 3:1 mixture of analytically pure acetone and solution of tris-(hydroxymethyl)-aminomethane,
  (b) clarifying the extract,
  (c) reacting the clarified extract with a solution of p-dimethylaminobenzaldehyde in analytically pure ethanol admixed with a strong acid,
  (d) determining the absorbance of the reacted extract at about 580 nm,
  (e) comparing the absorbance of the reacted extract with the absorbance at the same wavelength of a skatole solution of a preselected concentration in the same extraction agent and reacted with said p-dimethylaminobenzaldehyde solution and
  (f) detecting obnoxious taint on the basis of the determination in terms of skatole equivalents.

13. A method according to claim 12, wherein the process is carried out automatically and wherein the fat sample is minced and blended with a predetermined amount of extracting agent, the resulting extract is clarified, admixed with a predetermined amount of the colour reagent and, after a holding period to develop colour, is measured for absorbance at about 580 nm, and compared with a standard solution of skatole in the same extracting agent in which said standard solution also has been reacted with said p-dimethylaminobenzaldehyde solution to obtain measurement values directly in ppm skatole equivalents.

14. A rapid and reliable method of sorting out pig carcasses which are liable to develop boar taint when cooked, comprising the steps of:
  (a) taking fat samples from a plurality of pig carcasses,
  (b) extracting a fixed amount of each fat sample with an about 3:1 mixture of analytically pure acetone and a solution of tris-(hydroxymethyl) aminomethane in distilled water adjusted to a pH of about 7.5 and containing a reducing agent,
  (c) clarifying each extract,
  (d) reacting each clarified extract with a solution of p-dimethylaminobenzaldehyde in analytically pure ethanol admixed with a strong acid,
  (e) determining the absorbance of each reacted extract at about 580 nm,
  (f) comparing each said determined absorbance with the absorbance at the same wavelength of a skatole solution of a preselected concentration in the same extraction agent and reacted with the same colour reagent, to determine each fat sample's content in terms of skatole equivalents;
  (g) sorting out each carcass whose fat sample's content exceeds a threshold value lying in the range of from 0.15 to 0.30 ppm of skatole equivalents, steps (b) through (f) of said method of sorting out pig carcasses being completable in about 10 to 20 minutes.

15. A method according to claim 14, wherein each carcass whose fat sample's content is 0.25 ppm of skatole equivalents or above is sorted out.

16. A method according to claim 15, wherein the steps (a) through (f) are carried out automatically and wherein each fat sample is minced and blended with a predetermined amount of extracting agent, the resulting extract is clarified, admixed with a predetermined amount of the colour reagent and, after a holding period to develop colour, is measured for absorbance at about 580 nm, and compared with a standard solution of skatole in the same extracting agent and reacted with the same colour reagent to obtain measurement values directly in ppm skatole equivalents, and including the step of recording the measurement values.

* * * * *